United States Patent
Belthangady et al.

(10) Patent No.: US 9,907,495 B2
(45) Date of Patent: Mar. 6, 2018

(54) CONTINUOUS MONITORING OF TUMOR HYPOXIA USING NEAR-INFRARED SPECTROSCOPY AND TOMOGRAPHY WITH A PHOTONIC MIXER DEVICE

(71) Applicant: Verily Life Sciences LLC, Mountain View, CA (US)

(72) Inventors: Chinmay Belthangady, San Francisco, CA (US); Faisal Kashif, Irvine, CA (US); Seung Ah Lee, San Francisco, CA (US); Tamara Troy, San Francisco, CA (US); John D. Perreault, Mountain View, CA (US); Suresh Alla, San Jose, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 15/688,559

(22) Filed: Aug. 28, 2017

(65) Prior Publication Data

US 2017/0354359 A1 Dec. 14, 2017

Related U.S. Application Data

(62) Division of application No. 15/098,686, filed on Apr. 14, 2016.

(51) Int. Cl.
| | |
|---|---|
| *G01N 21/55* | (2014.01) |
| *A61B 5/1455* | (2006.01) |
| *A61B 5/145* | (2006.01) |
| *A61B 5/00* | (2006.01) |
| *H04N 5/372* | (2011.01) |

(Continued)

(52) U.S. Cl.
CPC ........ *A61B 5/14552* (2013.01); *A61B 5/0022* (2013.01); *A61B 5/14546* (2013.01); *H04N 5/33* (2013.01); *H04N 5/372* (2013.01); *H04N 5/374* (2013.01); *A61B 2562/0238* (2013.01)

(58) Field of Classification Search
CPC ........... G01N 21/6458; G01N 15/1434; G01N 15/1468; G01N 21/4795; G01N 27/228; G02B 21/0036; G02B 21/0024; G02B 27/4244; G02B 5/1828; G02B 26/001; G02B 5/32; G02B 6/29395; G01B 11/0641; G01B 11/002
See application file for complete search history.

(56) References Cited

U.S. PATENT DOCUMENTS

| | | | |
|---|---|---|---|
| 7,912,257 B2 * | 3/2011 | Paley .................. | A61B 5/4547 345/418 |
| 2004/0051926 A1 | 3/2004 | Gulden et al. | |
| 2006/0015021 A1 | 1/2006 | Cheng | |

(Continued)

OTHER PUBLICATIONS

PCT/US2017/025080, International Search Report and Written Opinion of the International Searching Authority, dated Jul. 28, 2017, 13 pages.

(Continued)

*Primary Examiner* — Michael P Stafira
(74) *Attorney, Agent, or Firm* — Christensen O'Connor Johnson Kindness PLLC

(57) ABSTRACT

A device and a method to measure the concentrations of oxygenated and deoxygenated hemoglobin in tissue around a tumor via near-infrared (NIR) spectroscopy with a photonic mixer device (PMD) is described.

12 Claims, 4 Drawing Sheets

(51) Int. Cl.
*H04N 5/33* (2006.01)
*H04N 5/374* (2011.01)

(56) References Cited

U.S. PATENT DOCUMENTS

| | | |
|---|---|---|
| 2007/0024946 A1 | 2/2007 | Panasyuk et al. |
| 2009/0048705 A1 | 2/2009 | Nubling et al. |
| 2011/0118572 A1 | 5/2011 | Bechtel et al. |
| 2014/0339438 A1 | 11/2014 | Correns et al. |
| 2014/0347676 A1 | 11/2014 | Velten et al. |
| 2015/0075067 A1 | 3/2015 | Stowe et al. |
| 2015/0287236 A1* | 10/2015 | Winne .................... G06F 3/147 382/128 |
| 2016/0086318 A1 | 3/2016 | Hannuksela et al. |

OTHER PUBLICATIONS

Ahmad Hassan et al, "Proof of Concept of Diffuse Optical Tomography Using Time-of-Flight Range Imaging Cameras," Proceedings of Electronics New Zealand Conference 2010, pp. 115-120, Hamilton, New Zealand, Nov. 2010, 6 pages.

* cited by examiner

CONTINUOUS MONITORING OF TUMOR HYPOXIA USING NEAR-INFRARED SPECTROSCOPY AND TOMOGRAPHY WITH A PHOTONIC MIXER DEVICE

CROSS REFERENCE TO RELATED APPLICATIONS

The present patent application is a divisional of U.S. application Ser. No. 15/098,686 filed on Apr. 14, 2016, which is incorporated herein by reference.

TECHNICAL FIELD

The present disclosure relates generally to continuous monitoring of the oxygenation of tissue, particularly tumor hypoxia, and more particularly, to a method and a device for calculating the concentrations of oxygenated and deoxygenated hemoglobin in tissue surrounding a tumor.

BACKGROUND DESCRIPTION

The microenvironment around a solid tumor is generally hypoxic. The ratio of deoxygenated to oxygenated hemoglobin concentration in tissue surrounding a tumor is higher than that in healthy tissue. By measuring tissue oxygenation, the functional behavior of a tumor may be assessed. Tissue oxygenation status may also be used to assess the effectiveness of conventional or neoadjuvant chemotherapies and to determine disease progression and aid in prognosis.

Near-infrared (NIR) absorption spectroscopy is a technique that has been used to measure the relative amounts of oxygenated and deoxygenated hemoglobin in tissue. In the NIR spectral window of 600-1000 nm, photon propagation in tissues is dominated by scattering rather than absorption. To make accurate measurements of hemoglobin concentration in the target tissue, the absorbed and scattered fractions of photons have to be decoupled. However, with continuous wave NIR absorption spectroscopy, which employs steady-state illumination, it is usually difficult to separate the absorbed and scattered fractions of photons. Therefore, conventional methods of NIR absorption spectroscopy do not allow accurate measurements of oxygenated and deoxygenated hemoglobin concentrations in tissue surrounding a tumor. To remedy this, researchers have developed various time- and frequency-domain techniques to measure the scattered and absorbed fractions of photons independently, and thereby calculate more accurate values of absolute hemoglobin concentrations. These measurement techniques that allow absorption and scattering to be measured separately are collectively referred to as Diffuse Optical Spectroscopy (DOS). When the scattered and absorbed fractions of photons are used for spatial reconstruction of tissue, the techniques are referred to as Diffuse Optical Tomography (DOT).

While there are commercially available continuous-wave NIR DOS devices (e.g. INVOS™ oximetry system from Medtronic-Covidien, NIRO-200NX Near Infrared Oxygenation Monitor from Hamamatsu, etc.), frequency domain NIR DOS devices have not transitioned from research to real-world use due to added complexities of the frequency domain techniques. The frequency domain DOS devices that are currently used for research are generally bulky and expensive, and therefore, cannot be easily translated into medical equipment for use in real-world hospital settings or at the point-of-care.

Thus, there remains a need to develop miniaturized, low-cost frequency domain spectroscopy and tomography devices that can be applied for continuous tissue oxygenation measurements.

SUMMARY

The present disclosure is directed to a device and a method for monitoring tumor hypoxia. The device and method of the present disclosure can be used for continuous monitoring of the functional status of tumors in patients undergoing chemotherapy. The device can be miniaturized so that it can be either implanted into a patient's body near a tumor, or the device can be mounted on a patient's body near a tumor site in the form of a wearable device. In some implementations, the device can be handheld such that it can be used at the point-of-care (e.g., at a patient's hospital bedside, in a physician's office, or at a patient's home) for evaluating the functional status of a tumor.

One aspect of the present disclosure is a device for continuous monitoring of a tumor in a tissue region. The device can comprise a PMD camera chip and at least one amplitude modulated near-infrared light source horizontally separated from the PMD camera chip, such that the PMD camera chip and the near-infrared light source are in a reflection geometry.

Another aspect of the present disclosure is a method for continuous monitoring of tumor hypoxia. The method comprises: a) illuminating a tissue region having a tumor with an amplitude modulated near-infrared light source provided in close proximity to the tumor; b) recording light reflected from the tissue region using a multi-pixel PMD camera chip provided in close proximity to the tumor, wherein the near-infrared light source is horizontally separated from the PMD camera chip; c) measuring amplitude and phase shift of the reflected light; d) calculating absorption and reduced scattering coefficients using the amplitude and phase shift of the reflected light; e) repeating steps a-d for at least two different wavelengths of light; and f) calculating the concentrations of oxygenated and deoxygenated hemoglobin in the tissue region using the absorption and reduced scattering coefficients calculated for the at least two different wavelengths of light.

Other embodiments of this disclosure are contained in the accompanying drawings, description, and claims. Thus, this summary is exemplary only, and is not to be considered restrictive.

BRIEF DESCRIPTION OF DRAWINGS

The accompanying drawings, which are incorporated in and constitute a part of this specification, illustrate the disclosed embodiments and together with the description, serve to explain the principles of the various aspects of the disclosed embodiments. The accompanying drawings are schematics and not necessarily drawn to scale. In the drawings.

Figure 1:
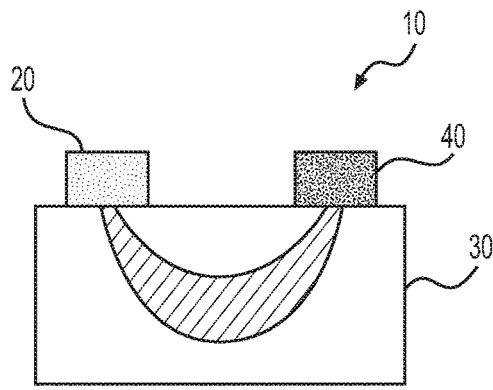
FIG. 1 is a schematic side view of a NIR spectroscopic device, according to an exemplary embodiment.

It is to be understood that both the foregoing general description and the following detailed description are exemplary and explanatory only and are not restrictive of the disclosed embodiments, as claimed.

DETAILED DESCRIPTION OF EXEMPLARY EMBODIMENTS

Reference will now be made to certain embodiments consistent with the present disclosure, examples of which are illustrated in the accompanying drawings. Wherever possible, the same reference numbers are used throughout the drawings to refer to the same or like parts.

The present disclosure describes a technique to measure the oxygenation status of tissue around a solid tumor via frequency domain NIR spectroscopy and tomography using a photonic mixer device (PMD). PMD is a semiconductor structure based on CCD- or CMOS-technology where each pixel comprises two charge storage locations (i.e., sub-pixels). Photoelectrons in the PMD are assigned alternately to the two sub-pixels as determined by a radiofrequency (RF) control voltage. The RF voltage signal is phase locked to a scene-illuminating light source that is modulated at the same frequency. The light reflected from the scene generates photoelectrons, which causes charge to build up at the two sub-pixels. The charge collected at the two sub-pixels gives the in-phase and 180° out-of-phase components of the reflected light signal. Using this information, the phase shift of the reflected light is calculated using Equation (1) shown below.

$$\text{Phase Shift} = 2\pi * \frac{V_Q}{(V_I + V_Q)} \quad (1)$$

where $V_I$ and $V_Q$ are the in-phase and out-of-phase components of the reflected light signal. The phase shift can be used to estimate the distance between the camera and the object that is being illuminated. When used for distance sensing, the PMD devices are often referred to as time-of-flight (ToF) cameras. In exemplary embodiments of the present disclosure, PMD-based ToF cameras can be used for measuring the amplitude and phase shift of reflected light signals, and the amplitude and phase shift values can then be used for measuring optical properties of biological tissue (instead of distance from the object being illuminated).

In exemplary embodiments, the amplitude and phase shift between the reflected and incident light can be used to measure tissue absorption and reduced scattering coefficients (μa and μs'), which can then be used to measure concentrations of oxygenated and deoxygenated hemoglobin. This is possible because absorption of light in tissue depends linearly on the concentrations of tissue chromophores (i.e., oxygenated hemoglobin, deoxygenated hemoglobin, water, lipids, etc.). The wavelength-dependent absorption coefficient is given by Equation (2) shown below.

$$\mu_a(\lambda) = \Sigma \epsilon_i(\lambda) C_i \quad (2)$$

Where $\epsilon_i(\lambda)$ is the wavelength-dependent extinction coefficient (usually known for typical tissue chromophores) and $C_i$ is the concentration of the ith chromophore. By measuring $\mu_a$ at multiple optical wavelengths, a system of coupled equations (equation (2)) is formed, which can then be solved to yield the unknown chromophore concentrations. Generally, to estimate the concentrations of N chromophores, one must determine $\mu_a$ at N or more wavelengths. Thus, in exemplary embodiments, to measure concentrations of oxygenated and deoxygenated hemoglobin, $\mu_a$ at two or more wavelengths is determined.

FIG. 1 shows a side view of an exemplary PMD-based NIR spectroscopic device 10 that can be used for determining optical properties of a biological tissue 30. Device 10 comprises a NIR light source 20 positioned in close proximity to a tumor site. In exemplary embodiments, NIR light source 20 can be a LED, fiber-couple laser, or a tunable laser emitting light at appropriate wavelengths. In exemplary embodiments, NIR light source 20 can emit light at a wavelength of about 600 nm to about 1000 nm. In some embodiments, two or more NIR light sources 20 can be used to emit light at different wavelengths. As previously discussed, to measure oxygenated and deoxygenated hemoglobin concentrations, phase and amplitude measurements at two wavelengths is required. Therefore, in some embodiments, two NIR light sources 20 can be used to emit light at two different wavelengths. In another embodiment, multiple NIR light sources 20 can be used to emit light of different wavelengths. Use of more wavelengths permits measurement redundancy, which in turn can improve the accuracy of hemoglobin concentration measurements.

Determination of hemoglobin concentrations requires the separation of tissue absorption from tissue scattering at more than one optical wavelength. In exemplary embodiments, wavelengths that minimize cross-talk between the oxygenated and deoxygenated hemoglobin can be chosen. For example, in some embodiments, at least one wavelength within the NIR window can be below the isosbestic point of hemoglobin (i.e., 800 nm) and one can be above this isosbestic point. For example, using only two wavelengths, a pair at about 780 nm and about 830 nm can be used. In some embodiments, a pair at about 660 nm and at about 940 nm can be used for the phase and amplitude measurements.

In exemplary embodiments, NIR light source 20 can be amplitude modulated at a frequency in the 10-1000 MHz range. For example, in some embodiments, NIR light source 20 can be amplitude modulated at 200 MHz. In another embodiment, NIR light sources can be amplitude modulated at 30 MHz.

Referring again to FIG. 1, NIR spectroscopic device 10 comprises a detector 40 positioned in close proximity to the tumor site. Detector 40 measures both phase and amplitude of the received modulated light relative to the incident light. In exemplary embodiments, device 10 can be operated in reflectance mode, such that NIR light source 20 and detector 40 are horizontally separated and positioned on the same side of the tissue, as shown in FIG. 1. The light reflected from the tissue is captured by detector 40. The crescent shaped region, shown in FIG. 1, is the sampled volume in the reflection geometry. When operated in transmittance mode, NIR light source 20 and detector 40 can be positioned on opposite sides of the tissue region, and light transmitted through the tissue is captured by detector 40. In the reflection geometry, light injected into the tissue from NIR light source 20 can be detected at a distance ρ by detector 40. In exemplary embodiments, the separation distance ρ between NIR light source 20 and detector 40 can be approximately twice the depth of the tumor from the tissue surface.

In exemplary embodiments, detector 40 can be a PMD-based ToF camera. In some embodiments, detector 40 can be a multi-pixel PMD camera chip. In such embodiments, the amplitude and phase shift information can be recorded at each pixel for different modulation frequencies of NIR light source 20 and detector 40. The amplitude and phase shift information can then be used to estimate the real and imaginary parts of the complex wavevector (k) associated with the diffuse photon density waves in the medium. In an exemplary embodiment comprising an infinite, homogeneous turbid media, the fluence rate (U(r)) of the diffuse photon density waves can be written as:

$$U(r) = \frac{\partial S_{ac}}{4\pi D r} \exp(-kr) \quad (3)$$

The complex wavefactor k is defined as $k = k_r + ik_i$ and $k^2 = (-\theta\mu_a + iw)/D$, where $\theta$ is the speed of light in the medium, D is the photon diffusion coefficient and $D = \theta/3 (\mu_s' + \mu_a)$. The reflectance amplitude at a distance r from the light source is equal to $k_r * r$, while the phase shift at a distance r from the light source is equal to $k_i * r$. From the complex wavevector (k), absorption coefficient $\mu_a$ and reduced scattering coefficient $\mu_s'$ can be calculated using equation (3).

In exemplary embodiments, the absorption and scattering coefficients ($\mu_a$ and $\mu_s'$, respectively) recorded at multiple light wavelengths can be used to calculate the concentrations of oxygenated and deoxygenated hemoglobin. For example, in some embodiments, equation (2) can be used to calculate the hemoglobin or any other chromophore concentration.

Figure 2:
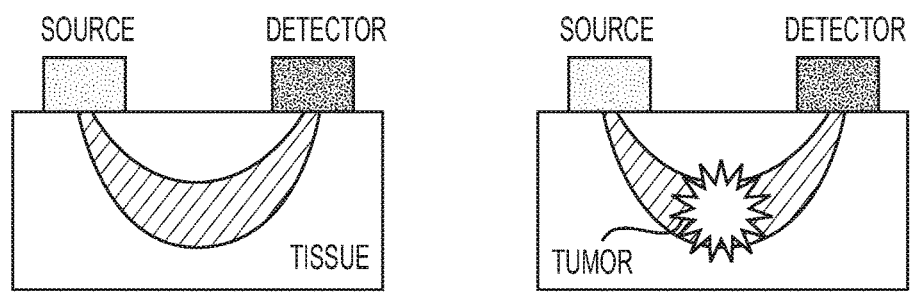
FIG. 2 shows the time delay and phase shift of reflected light as a result of a tumor in the sampled volume of a tissue region, according to an exemplary embodiment.
Figure 2:
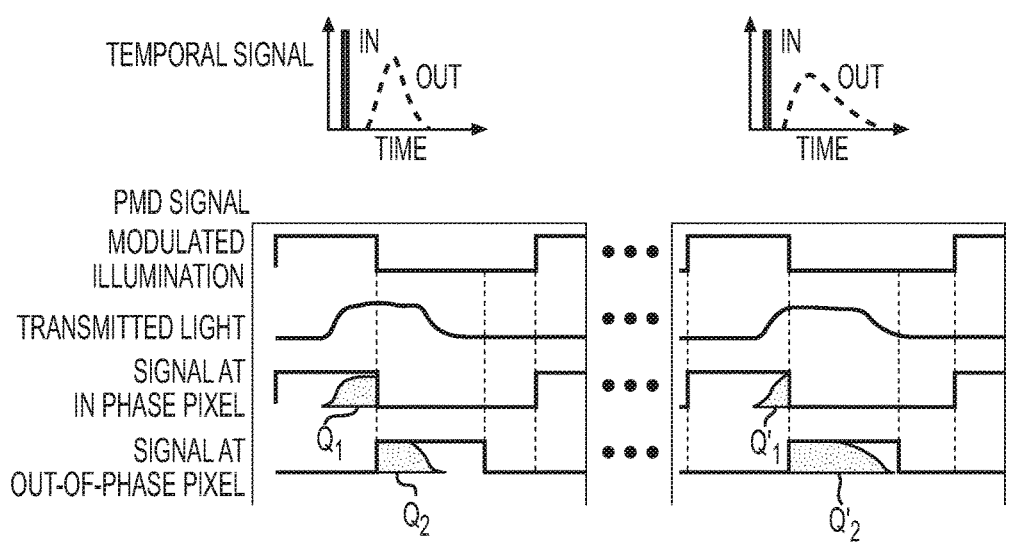

FIG. 2 illustrates the effect of a tumor in the sampled volume of a tissue region. Presence of a solid tumor can cause more light scattering and delay in light reaching detector 40, which is turn can cause phase shift between the incident and reflected light. The charge collected at the two sub-pixels is shown as $Q_1$, $Q'_1$ and $Q_2$, $Q'_2$ in FIG. 2. The phase shift is registered as an increase in charge ($Q_2'$) at the second charge storage location (i.e., the out-of-phase pixel). The amount of phase shift can be calculated from the charges collected at the two charge locations. The amplitude and phase shift can be recorded at each pixel of PMD-based detector 40 for different modulation frequencies.

Figure 3:
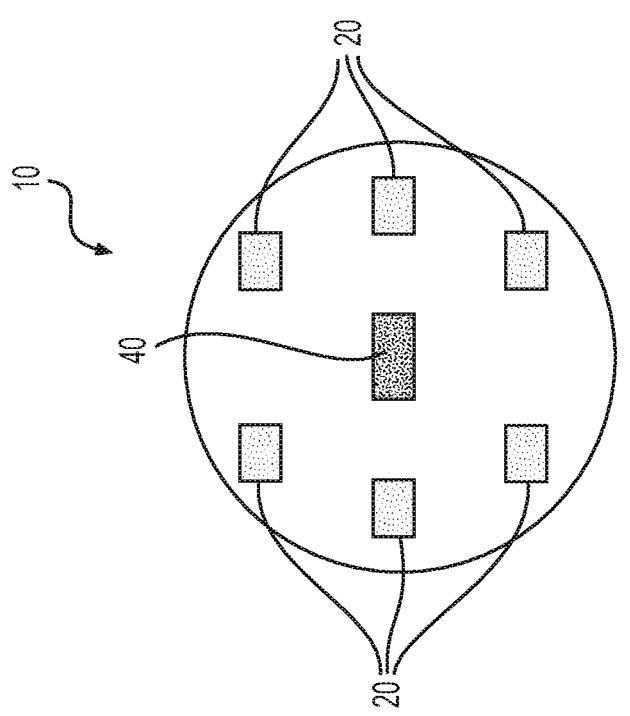
FIG. 3 is a schematic top view of a NIR spectroscopic device, according to an exemplary embodiment.

In exemplary embodiments comprising a multi-pixel PMD camera chip as detector 40, coarse structural and positional information of the tumor can also be determined by using tomographic reconstruction algorithm. In some embodiments, multiple NIR light sources 20 can be arranged in an array around the PMD-based detector 40, as shown in FIG. 3. In another embodiment, one or more NIR light sources 20 are mounted with a motor to move the light source around the PMD-based detector 40. In exemplary embodiments, multiple NIR light sources 20 can be operated in a multiplexed fashion (either time division or frequency division) such that the amplitude and phase signal for each source is separately recorded. The information recorded can then be used to tomographically reconstruct the spatial distribution of absorbers and scatterers within the tissue medium, thereby getting information on the size, structure and position of the tumor.

Figure 5:
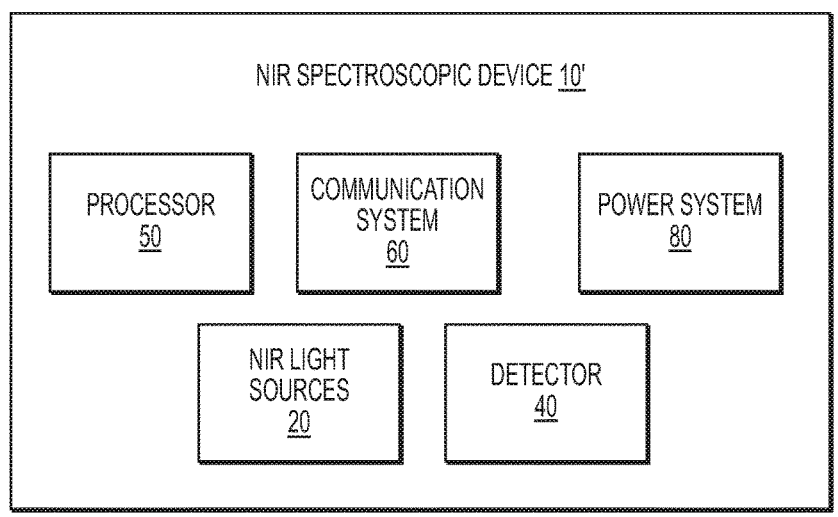
FIG. 5 is a schematic diagram of a NIR spectroscopic device, according to an exemplary embodiment.

FIG. 5 shows a schematic diagram of a NIR spectroscopic device 10', according to an exemplary embodiment. Due to the small form factors of PMD ToF cameras, device 10' can be implemented as a handheld device, a wearable device, or an implantable device. Device 10' can include a processor 50, a communication system 60, and a power system 80 in addition to NIR light sources 20 and detector 40. Processor 50 can control the overall operation of device 10'. Processor 50 can also process and/or analyze the recorded phase and amplitude data and determine an oxygenation status of the target tissue. Communication system 60 can comprise wired or wireless communication capabilities, including antennas, transceivers, encoders, decoders, etc. In some embodiments, communication system 60 can transmit the processed data to a remote storage device or a remote display device where the oxygenation status can be displayed. In some embodiments, communication system 60 can transmit raw data to a remote processing device or a cloud server, where calculations can be performed and the results can be transmitted to the patient or a healthcare provider. In some embodiments, device 10' can include on-chip electronics to pre-process the recorded data prior to processing by processor 50, or prior to transmission to the remote processing device or cloud server. In such embodiments, device 10' can include amplifiers, analog-to-digital converters, multiplexers, and other electronic circuitry to pre-process the acquired data. The power system 80 can power processing system 50, communication system 60, NIR light sources 20 and detector 40. In some embodiments, device 10' can be wirelessly powered. In such embodiments, power system 80 can include a supercapacitor, a battery, or some other type of charging system that can be charged wirelessly by a remote device. In some embodiments, optical powering using an array of photovoltaic cells can be used to power the embedded electronics of device 10' or recharge its battery.

Example: Application of PMD-ToF Camera for Phase Shift Measurements

Figure 4:
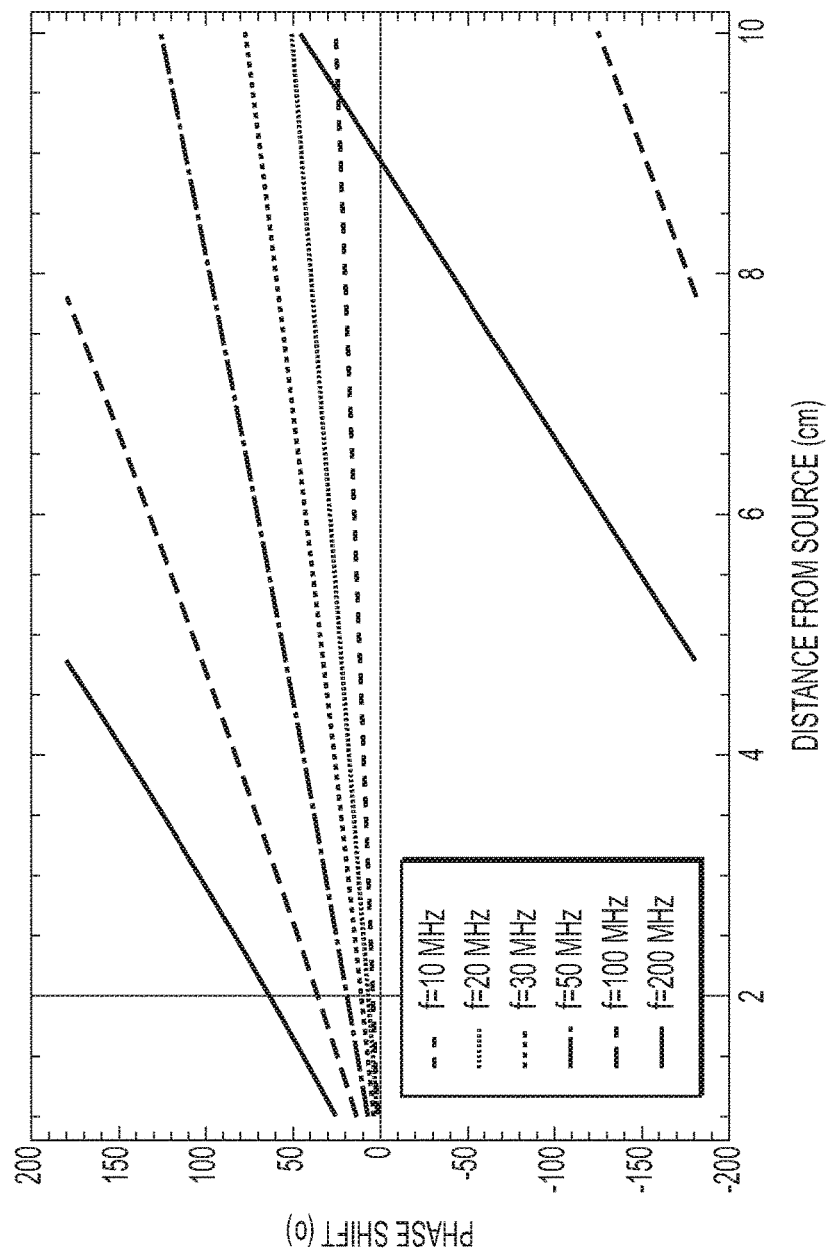
FIG. 4 is a chart showing phase shifts computed at different modulation frequencies and at different source-detector separations, according to an exemplary embodiment.

Phase shift between incident and reflected light was computed for many different modulation frequencies in a semi-infinite medium (with optical properties similar to tissue) in order to verify that representative phase shifts are measurable using a PMD ToF camera. FIG. 4 shows the phase shifts for different modulation frequencies (f) at different source-detector separations p. The results indicate that as source-detector separation increases, the phase shift increase. As an example, when $\rho = 5$ cm and $f = 30$ MHZ, the phase shift is 35°, which corresponds to a time delay of ~3 ns. When used for distance sensing, time delay of ~3 ns corresponds to a camera-to-object distance of 45 cm, which can be detected by a PMD ToF camera, thus implying that a corresponding phase shift of 35° can also be detected by a PMD ToF camera.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiment. Moreover, while illustrative embodiments have been described herein, the disclosure includes the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods can be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A method for continuous monitoring of tumor hypoxia, the method comprising:
   illuminating a tissue region having a tumor with an amplitude modulated near-infrared light source provided in close proximity to the tumor;
   recording light reflected from the tissue region using a multi-pixel PMD camera chip provided in close proximity to the tumor, wherein the near-infrared light source is horizontally separated from the PMD camera chip;
   measuring amplitude and phase shift of the reflected light;
   calculating absorption and reduced scattering coefficients using the amplitude and phase shift of the reflected light;
   repeating steps a-d for at least two different wavelengths of light; and
   calculating the concentrations of oxygenated and deoxygenated hemoglobin in the tissue region using the absorption and reduced scattering coefficients calculated for the at least two different wavelengths of light.

2. The method of claim 1, wherein the tissue region is illuminated with multiple near-infrared light sources arranged around the PMD camera chip.

3. The method of claim 2, wherein the multiple infrared light sources are operated in a multiplexed fashion such that the amplitude & phase shift for each light source is recorded separately.

4. The method of claim 1, wherein a first wavelength of the at least two wavelengths of light is above the isosbestic point of hemoglobin and a second wavelength of the at least two wavelengths of light is below the isosbestic point of hemoglobin.

5. The method of claim 4, wherein the first wavelength is about 780 nm and the second wavelength is about 830 nm.

6. The method of claim 1, wherein the near-infrared light source is modulated at a frequency in the 10-1000 MHz range.

7. The method of claim 6, wherein the near-infrared light source is modulated at a frequency of 30 MHz.

8. The method of claim 6, wherein the near-infrared light source is modulated at a frequency of 200 MHz.

9. The method of claim 1, where the amplitude and phase shift values are wirelessly transmitted to a cloud server for calculating the absorption and reduced scattering coefficients and the concentrations of oxygenated and deoxygenated hemoglobin.

10. The method of claim 1, wherein the modulated near-infrared light source and the PMD camera chip are positioned at a distance approximately twice the depth of the tumor from the surface of the tissue region.

11. The method of claim 1, wherein the near-infrared light source and the PMD camera chip are wirelessly powered.

12. The method of claim 1, wherein the near-infrared light source is rotated around the PMD camera chip.

* * * * *